US008796029B2

(12) United States Patent
Chung et al.

(10) Patent No.: US 8,796,029 B2
(45) Date of Patent: Aug. 5, 2014

(54) SYSTEM AND METHOD FOR PROCESSING TARGET MATERIAL

(75) Inventors: Won Seok Chung, Hwaseong-si (KR); Kak Namkoong, Seoul (KR); Joonho Kim, Seongnam-si (KR); Kyuyoun Hwang, Yongin-si (KR); Heekyun Lim, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 855 days.

(21) Appl. No.: 12/415,262

(22) Filed: Mar. 31, 2009

(65) Prior Publication Data

US 2010/0130732 A1    May 27, 2010

(30) Foreign Application Priority Data

Nov. 27, 2008  (KR) ...................... 10-2008-0119079

(51) Int. Cl.
*G01N 35/00*  (2006.01)
*G01N 33/53*  (2006.01)
*G01N 33/48*  (2006.01)
*G01N 21/07*  (2006.01)

(52) U.S. Cl.
CPC ............... *G01N 33/53* (2013.01); *G01N 33/48* (2013.01); *G01N 21/07* (2013.01); *G01N 2035/00495* (2013.01); *G01N 2035/00099* (2013.01); *G01N 2035/00158* (2013.01); *G01N 2035/00148* (2013.01); *B01L 2400/0409* (2013.01)
USPC ................. 436/45; 436/86; 422/64; 422/68.1

(58) Field of Classification Search
CPC .......... G01N 2035/00148; G01N 2035/00158; G01N 2035/0099
USPC ................................ 422/64, 68.1; 436/45, 86
See application file for complete search history.

(56) References Cited

U.S. PATENT DOCUMENTS

| 4,430,299 | A  | * | 2/1984 | Horne ............................ 422/64 |
| 6,706,519 | B1 | * | 3/2004 | Kellogg et al. ............ 435/287.2 |
| 7,322,254 | B2 |   | 1/2008 | Bedingham et al. |
| 2009/0035847 | A1 | * | 2/2009 | Cho et al. ................... 435/289.1 |

FOREIGN PATENT DOCUMENTS

| JP | 2006-223252 | 8/2006 |
| JP | 2008-017842 | 1/2008 |
| KR | 1020080022035 | 3/2008 |
| KR | 1020080090667 | 10/2008 |

OTHER PUBLICATIONS

Morier et al., Electrophoresis, 2004,25,3761-3768.*

* cited by examiner

*Primary Examiner* — Lyle Alexander
(74) *Attorney, Agent, or Firm* — Cantor Colburn LLP

(57) ABSTRACT

A system for processing a target material includes; a cartridge which stores a material which reacts with the target material, and may include at least one chamber and at least one valve connected to the at least one chamber, a first module which may be loaded with the at least one cartridge and may rotate, a second module which may selectively open or close the at least one valve, a third module which may selectively control the temperature of the at least one chamber, and a control module which may control the first module, the second module and the third module.

18 Claims, 8 Drawing Sheets

SYSTEM AND METHOD FOR PROCESSING TARGET MATERIAL

CROSS-REFERENCE TO RELATED APPLICATION

This application claims priority to Korean Patent Application No. 10-2008-119079, filed on Nov. 27, 2008, and all the benefits accruing therefrom under 35 U.S.C. §119, the contents of which in its entirety are herein incorporated by reference.

BACKGROUND

1. Field

Exemplary embodiments relate to a system for processing a target material and a method for processing a target material.

2. Description of the Related Art

Recently, molecular diagnosis techniques utilizing nucleic acids are on the increase. The molecular diagnosis techniques based on nucleic acids may be applied for detecting infectious diseases or cancers, or in the field of pharmacogenomics. An automated nucleic acid extraction system may be used as a means to extract nucleic acids. Existing nucleic acid extraction systems include systems using microparticle-based reagents, such as magnetic beads, and devices which extract nucleic acid utilizing e-tubes equipped with filters.

SUMMARY

Exemplary embodiments provide a system and a method for automated processing of a target material, e.g., extracting a specific target material from a sample.

According to an exemplary embodiment, a system for processing a target material includes; a cartridge which stores a material which reacts with the target material, and which may comprise at least one chamber and at least one valve connected to the at least one chamber, a first module which may be loaded with the at least one cartridge and may rotate, a second module which may selectively control the at least one valve, a third module which may selectively control the temperature of the at least one chamber, and a control module which may control the first module, second module and third module.

According to another exemplary embodiment, a method for processing a target material includes; injecting a material which reacts with the target material in a cartridge comprising at least one chamber and at least one valve connected to the at least one chamber, injecting a sample including the target material into the cartridge, rotating the cartridge, selectively controlling the at least one valve connected to the at least one chamber to transfer the target material from the at least one chamber, and selectively controlling the temperature of the at least one chamber.

According to still another exemplary embodiment, a method for processing a target material includes; injecting a lysis buffer, a binding buffer containing micro particles, a washing buffer and an elution buffer in a lysis chamber, a binding chamber, a washing chamber and an elution chamber of a cartridge, respectively, injecting a sample including the target material into the lysis chamber; heating the lysis chamber, transferring the sample to the binding chamber, binding the target material to the micro particles, collecting the micro particles and bound target material in a collection chamber, heating the elution chamber, transferring the heated elution buffer from the elution chamber to the collection chamber, separating the target material from the micro particles, and collecting a fluid including the separated target material in an eluate chamber.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION

Figure 1:
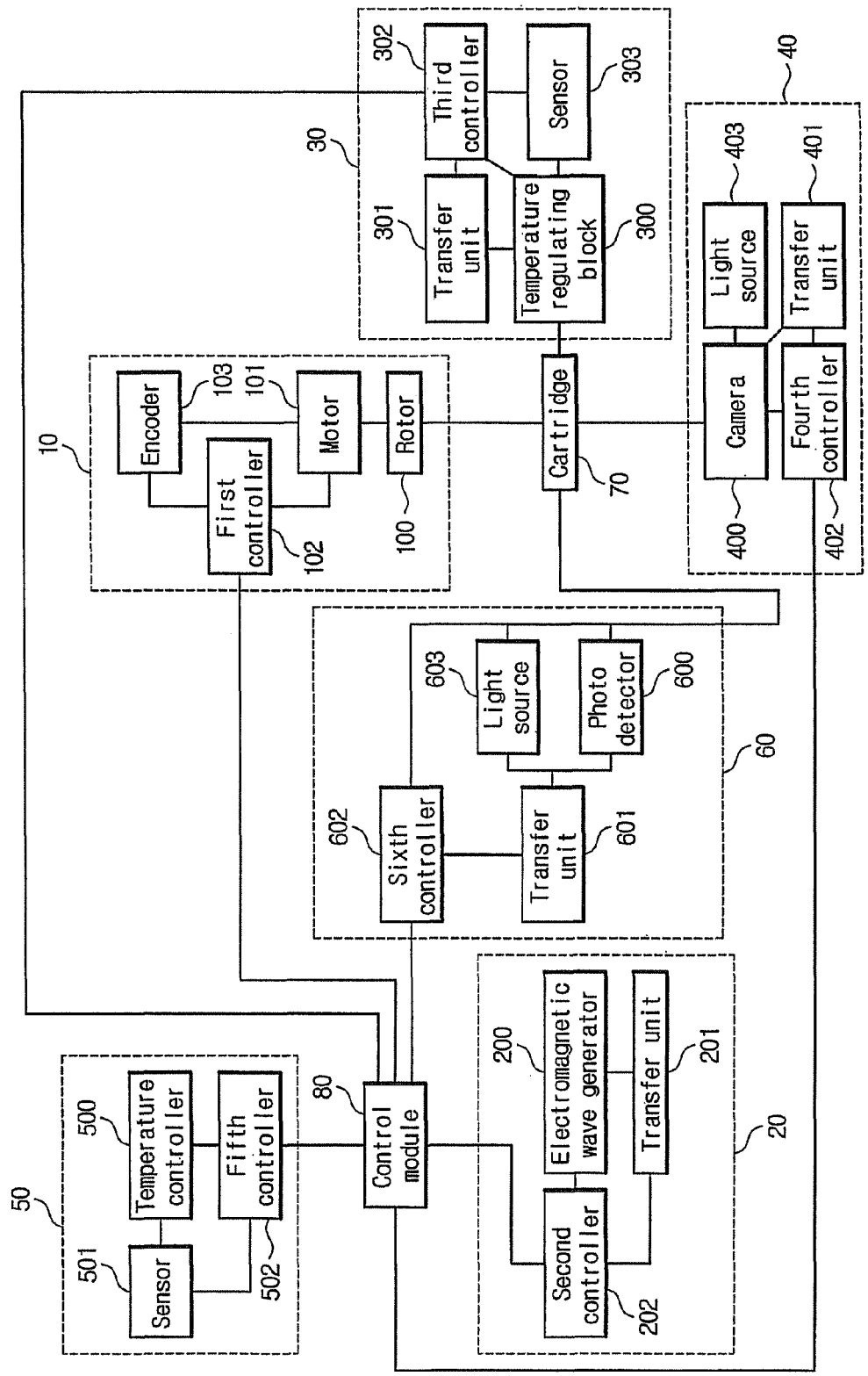
FIG. 1 is a block diagram of an exemplary embodiment of a system for processing a target material.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. Like reference numerals refer to like elements throughout. In the description, details of well-known features and techniques may be omitted to avoid unnecessarily obscuring the presented embodiments. The shape, size and regions, and the like, of the drawing may be exaggerated for clarity.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. do not denote a limitation of quantity, but rather denote the presence of at least one of the referenced item. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

FIG. 1 is a block diagram of an exemplary embodiment of a system for processing a target material.

Referring to FIG. 1, a system for processing a target material may include a cartridge 70, a first module 10, a second module 20, a third module 30, and a control module 80. A sample including the target material and a reagent reacting with the target material may be injected in the cartridge 70. The target material is not limited to a particular kind. For example, the target material may include nucleic acid, protein, peptide, antibody, hormone, other suitable materials or a combination thereof. The nucleic acid may include DNA or RNA. Exemplary embodiments of the sample including the target material include cell suspension, blood, urine, saliva, other suitable materials or a combination thereof. The cartridge 70 may be made of plastic, metal, polymer, other suitable materials, or a combination thereof. The cartridge 70 may comprise at least one chamber and at least one valve connected to the chamber. In the exemplary embodiment wherein the cartridge includes multiple chambers, the at least one valve may be disposed between the respective chambers. The structure of the cartridge 70 will be described in detail later referring to FIGS. 2A to 2C.

The first module 10 may be loaded with the at least one cartridge 70 and may rotate. As the first module 10 loaded with the cartridge 70 rotates, the materials contained in the cartridge 70 may be mixed with each other or may react with each other, e.g., through physical agitation. For example, nucleic acids included in a sample may be reacted with a reagent in the cartridge 70.

In one exemplary embodiment, the first module 10 may comprise a rotor 100 and a motor 101. The at least one cartridge 70 may be mounted on the rotor 100. The rotor 100 may be connected to the motor 101, and may be rotated by a driving force provided by the motor 101. Exemplary embodiments of the motor 101 may include a step motor, a direct current ("DC") motor, an alternating current ("AC") motor or other suitable motors.

The first module 10 may further include a first controller 102 and an encoder 103. The encoder 103 may be connected to the motor 101 and may generate a signal corresponding to the rotation of the motor 101. In one exemplary embodiment, the encoder 103 may include an optical encoder and/or a magnetic encoder. The signal may correspond to one or more characteristics of the rotation of the motor 101, including rotating speed, rotating angle, rotating direction, or other related variables of the motor 101. The first controller 102 may be controlled by the control module 80, may generate a control signal, exemplary embodiments of which include a pulse signal, to control the motor 101 using a signal received from the encoder 103, and may control the motor 101 using the control signal. In one exemplary embodiment, the first controller 102 may control rotating speed, rotating angle, rotating direction, etc. of the motor 101.

The second module 20 may open or close the valve included in the cartridge 70. As a result, it may control a flow of the sample, so that the target material may be positioned in a desired chamber among the at least one chamber of the cartridge 70. Further, it may transfer the reagents stored in the cartridge 70 to a desired chamber.

The second module 20 may include an electromagnetic wave generator 200. In one exemplary embodiment, the electromagnetic wave generator 200 may open or close the valve included in the cartridge 70 by irradiating the valve with an electromagnetic wave. However, in an exemplary embodiment wherein the valve in the cartridge 70 is operated by a power source other than electromagnetic wave, the second module 20 may comprise a different valve operation means.

The second module 20 may further comprise a transfer unit 201 and a second controller 202. The transfer unit 201 may be controlled by the second controller 202, and may have the electromagnetic wave generator 200 mounted thereon. The second controller 202 may control the transfer unit 201 and the electromagnetic wave generator 200 under the control of the control module 80, so that a desired valve in the cartridge 70 may be opened or closed.

The third module 30 may control the temperature of any of the at least one chamber in the cartridge 70. Specifically, if more than one chamber is included in the cartridge 70, the temperature of the individual chambers may be independently controlled. Depending on the kinds of the target material and reagent, a particular temperature may be optimal for the processing of the target material. As the temperature of the corresponding chamber in the cartridge 70 may be controlled by the third module 30, a desired reaction of the target material may occur.

The third module 30 may comprise a temperature regulating block 300, a transfer unit 301, a third controller 302 and a sensor 303. The temperature regulating block 300 may control the temperature of the at least one chamber included in the cartridge 70. In one exemplary embodiment, the temperature regulating block 300 may comprise a Peltier element or other suitable heating or cooling means. The transfer unit 301 may include the temperature regulating block 300 mounted thereon and may be moved with respect to the cartridge 70. The sensor 303 may measure the temperature of the temperature regulating block 300. The third controller 302 may be controlled by the control module 80, and may control the operation of the temperature regulating block 300 depending on the temperature measured by the sensor 303. Further, the third controller 302 may control the transfer unit 301, so that the temperature regulating block 300 may be positioned in proximity to a desired chamber of the cartridge 70.

The system for processing a target material may further comprise a fourth module 40 for monitoring the target material processing procedure in the cartridge 70. In one exemplary embodiment, the fourth module 40 may include a camera 400 for photographing the cartridge 70. The image photographed by the camera 400 may be transferred to the control module 80. The fourth module 40 may further comprise a transfer unit 401, a fourth controller 402 and a light source 403. The camera 400 may photograph the cartridge 70 while the light source 403 periodically applies light to the cartridge 70. In one exemplary embodiment, the light source 403 may be a stroboscope. The fourth controller 402 may be controlled by the control module 80, and may control the camera 400 and the transfer unit 401, so that the position and operation of photographing may be controlled.

The system for processing a target material may further comprise a fifth module 50 which controls the temperature of substantially the whole cartridge 70. When some materials, such as RNA, are used as the target material or the sample it may be optimal to maintain the temperature of substantially the whole cartridge 70 at a constant temperature. The fifth module 50 may control the temperature of substantially the whole cartridge 70 at a predetermined temperature. The fifth module 50 may comprise a temperature controller 500, a sensor 501 and a fifth controller 502. The sensor 501 may measure the temperature of the temperature controller 500. The fifth controller 502 may be controlled by the control module 80, and may control the temperature controller 500 depending on the temperature measured by the sensor 501, so that the temperature of substantially the whole cartridge 70 may be controlled at a predetermined temperature. In another exemplary embodiment, the fifth module 50 may control the temperature of the entire system, including the cartridge 70, at a predetermined temperature.

The system for processing a target material may further comprise a sixth module 60 which measures a concentration of the target material in an optical manner. In the exemplary embodiment wherein the target material is nucleic acid, an optimal reagent may be added to the chamber containing the nucleic acid after nucleic acid extraction has been completed, and polymerase chain reaction ("PCR") may be performed using the third module 30. Meanwhile, the concentration of the amplified nucleic acid in the chamber may be monitored in real time using the sixth module 60.

The sixth module 60 may comprise a photo detector 600, a transfer unit 601, a sixth controller 602 and a light source 603. The transfer unit 601 may transfer the light source 603 and the photo detector 600, so that they may be positioned in proximity to a desired chamber of the cartridge 70. In one exemplary embodiment, the desired chamber may be a chamber in which PCR is carried out. The light source 603 may apply light to the corresponding chamber. The photo detector 600 may detect fluorescence emitted from the corresponding chamber to measure the nucleic acid concentration in the chamber. The sixth controller 602 may be controlled by the control module 80, and may control the operation of the light source 603, the photo detector 600 and the transfer unit 601.

The control module 80 may control the first to sixth modules 10, 20, 30, 40, 50, 60. In one exemplary embodiment, the control module 80 controls the first to sixth modules 10, 20, 30, 40, 50 and 60 by controlling the first to sixth controllers 102, 202, 302, 402, 502, 602, respectively. The control module 80 may send and receive signals to and from the first to sixth controllers 102, 202, 302, 402, 502, 602 using wired or wireless communication. In one exemplary embodiment, the control module 80 may control the respective modules 10, 20, 30, 40, 50, 60 according to a preset target material processing procedure. In one exemplary embodiment, the control module 80 may comprise a computational device, such as a computer.

Figure 2A:
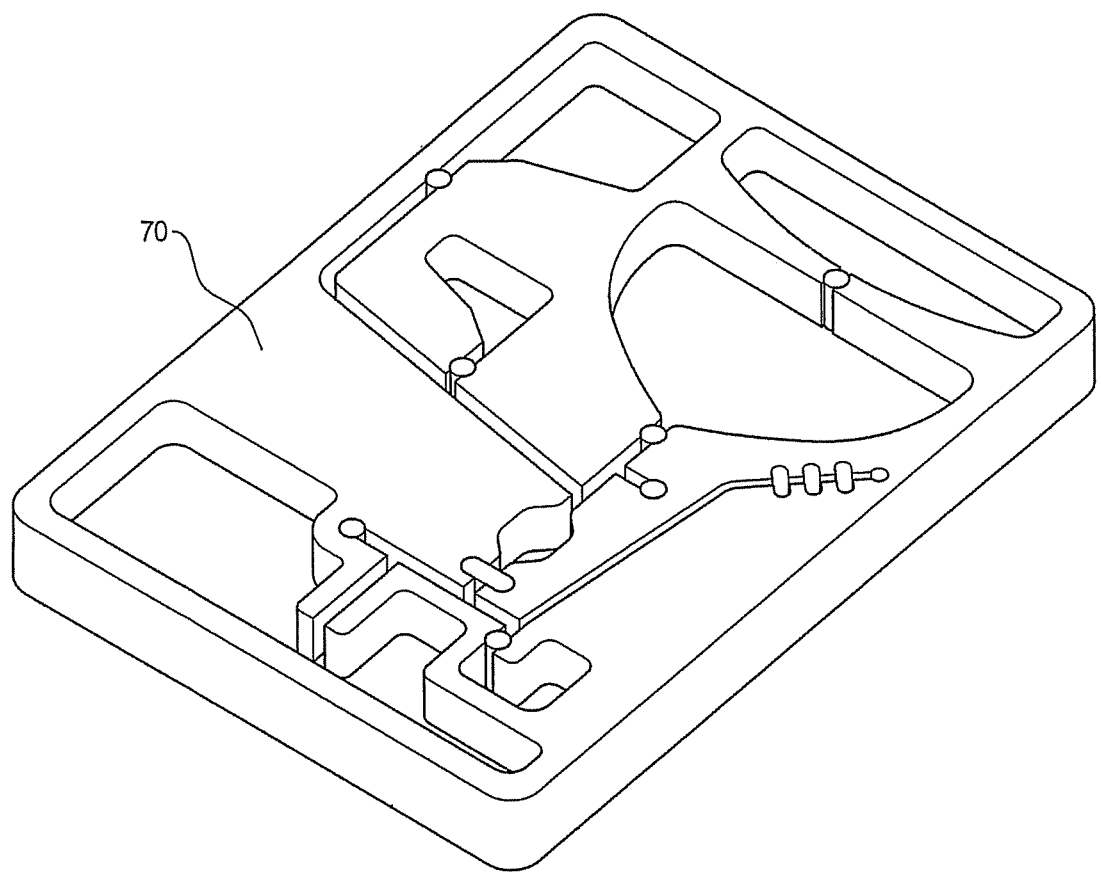
FIG. 2A is a front perspective view of an exemplary embodiment of a cartridge included in an exemplary embodiment of a system for processing a target material.

FIG. 2A is a front perspective view of an exemplary embodiment of a cartridge included in an exemplary embodiment of a system for processing a target material. Referring to FIG. 2A, the cartridge 70 may have a shape of a plate, or a substrate, having at least one chamber. In one exemplary embodiment, the at least one chamber may be formed by etching out portions of the cartridge 70. The chambers may be connected by channels, and the flow of fluid through the channels may be controlled by at least one valve. The cartridge 70 may further have an additional plate 72 (see FIG. 2C) for covering the plate on which the chamber, the channel and the valve are formed. In one exemplary embodiment, each plate of the cartridge 70 may be made of a transparent material.

Figure 2B:
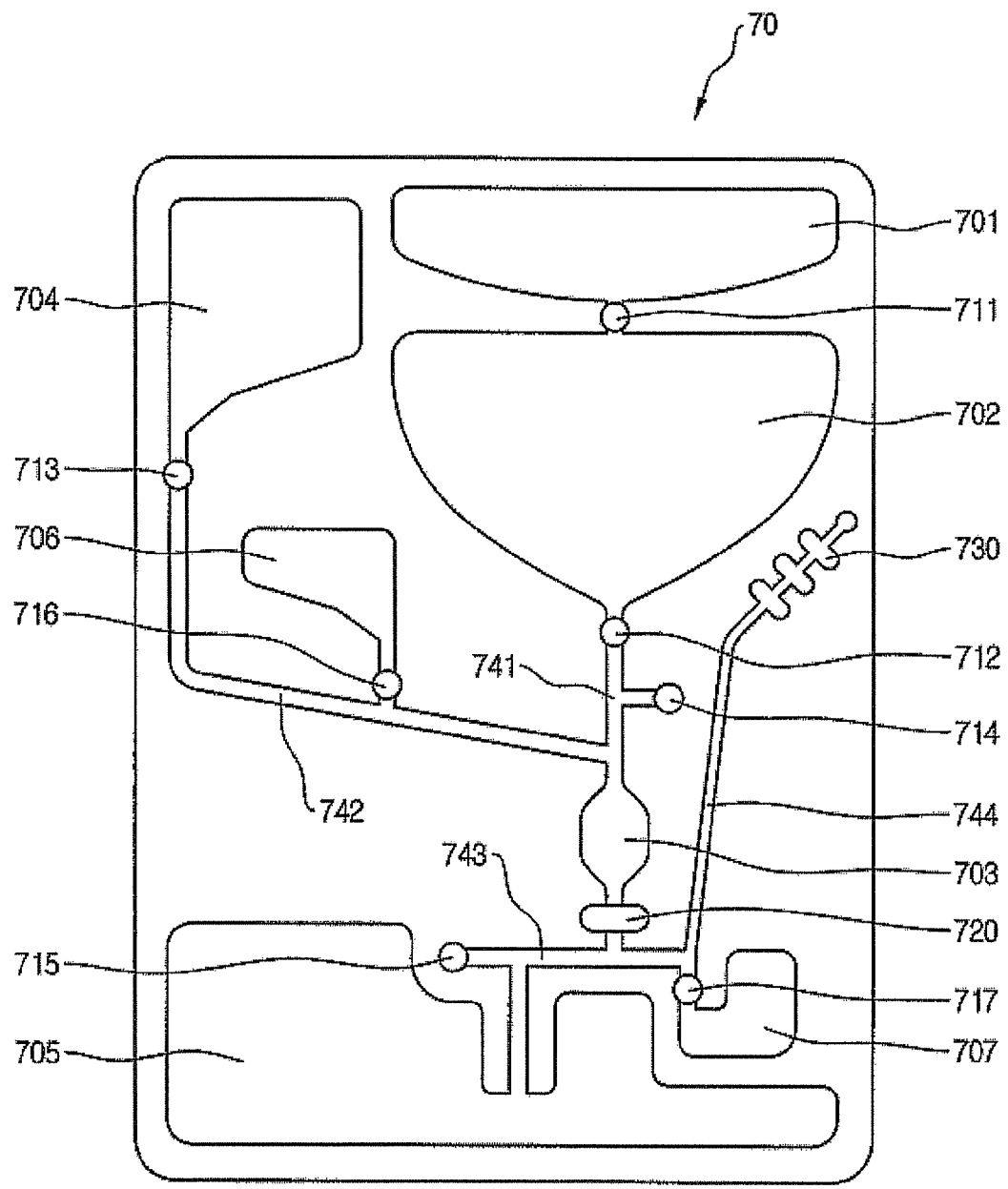
FIG. 2B is a plan view of the exemplary embodiment of a cartridge illustrated in FIG. 2A.

FIG. 2B is a plan view of the exemplary embodiment of a cartridge 70 illustrated in FIG. 2A. Referring to FIG. 2B, the cartridge 70 may include a lysis chamber 701, a binding chamber 702, a collection chamber 703, a washing chamber 704, a waste chamber 705, an elution chamber 706 and an eluate chamber 707. The respective chambers may be connected to each other by channels 741, 742, 743, 744.

The flow of fluid through the channels 741-744 may be controlled by first to seventh valves 711-717. The first to third valves 711, 712, 713, the sixth valve 716, and the seventh valve 717 may be opening valves. An opening valve may refer to a valve which normally blocks the flow of fluid but allows fluid to flow through when open. In one exemplary embodiment the first to third valves 711, 712, 713, the sixth valve 716, and the seventh valve 717 may be opened by absorbing externally supplied energy. That is, the first to third valves 711, 712, 713, the sixth valve 716, and the seventh valve 717 may be controlled, so that fluid may flow through the channels connected to the respective valves. The fourth and fifth valves 714, 715 may be closing valves. A closing valve may refer to a valve which normally allows the flow of fluid but blocks the flow of fluid therethrough when closed. In one exemplary embodiment the fourth and fifth valves 714, 715 are closed by absorbing external energy. That is, the fourth and fifth valves 714, 715 may be controlled, so that the flow of fluid through the channels connected to the respective valves may be blocked.

Figure 2C:
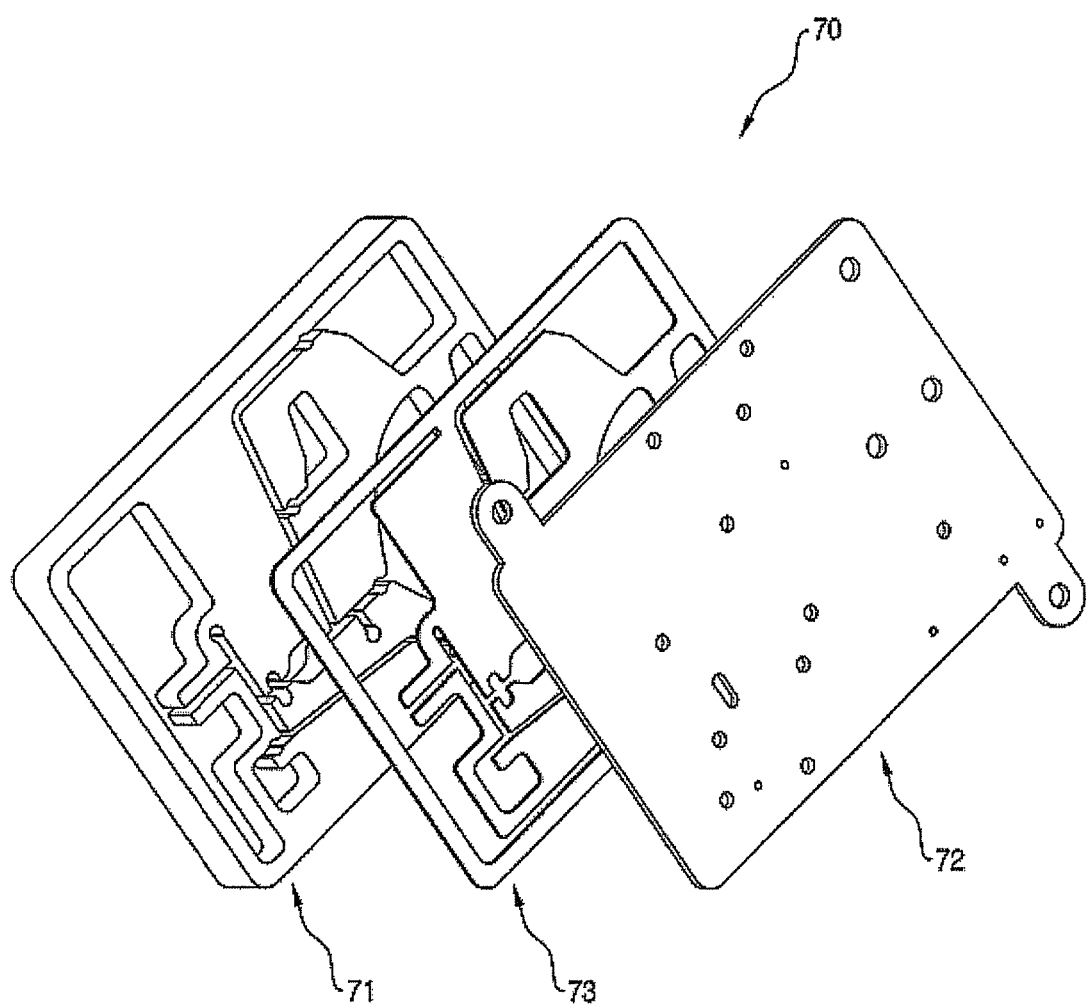
FIG. 2C illustrates an exemplary embodiment of a method of fabricating a cartridge using double-sided tape.

FIG. 2C illustrates an exemplary embodiment of a method of fabricating the cartridge 70. Referring to FIG. 2C, the cartridge 70 may be fabricated by fabricating a lower plate 71 and an upper plate 72, respectively, and bonding the lower plate 71 and the upper plate 72 using double-sided tape 73. In one exemplary embodiment, the lower plate 71 and the upper plate 72 may be fabricated by processing a polycarbonate plate using a computer numerical control ("CNC") machine or by other suitable methods.

Figure 3A:
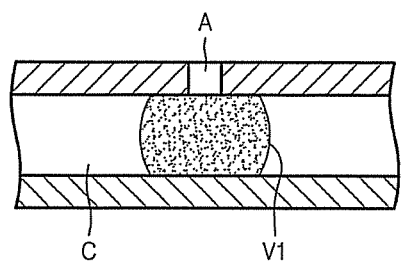
FIGS. 3A and 3B illustrate an exemplary operation of an opening valve.
Figure 3B:
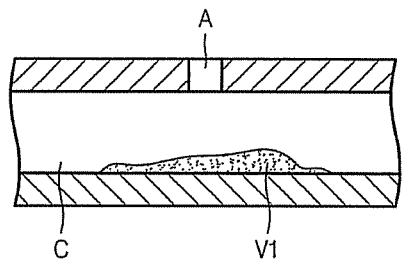

FIGS. 3A and 3B are cross-sectional views illustrating an exemplary operation of an opening valve. Referring to FIG. 3A, an opening valve may comprise a valve material V1 which is solidified at normal temperature, e.g., an ambient temperature or a room temperature. The valve material V1 may be injected through an injection hole A and then may be solidified. The valve material V1 may close a channel C to block the flow of fluid therethrough when it is in a solidified state before it absorbs externally supplied energy, e.g., from an electromagnetic wave.

Referring to FIG. 3B, the valve material V1 may be melted when it absorbs externally supplied energy, e.g., from an electromagnetic wave. In one exemplary embodiment, the valve material V1 may be melted at high temperature. As the valve material V1 is melted and transferred to a space in the channel C, the channel C may be opened.

In one exemplary embodiment, the valve material V1 may comprise a phase change material ("PCM") which is in solid state at a normal temperature, e.g., a room-temperature. Exemplary embodiments of the PCM include wax, gel, thermoplastic, or other suitable materials. In one exemplary embodiment, the valve material V1 may include microcrystalline wax, natural wax, synthetic wax, ferrowax, or other suitable materials.

In one exemplary embodiment, the energy applied to the valve material V1 may be an electromagnetic wave. The second module 20 in the system for processing a target material may include a device for applying an electromagnetic wave such as the electromagnetic wave generator 200. In one exemplary embodiment, the second module 20 may include a laser light source which irradiates a laser beam, a light emitting diode ("LED") which irradiates visible or infrared light, a xenon lamp, or other suitable mechanisms for generating an electromagnetic wave. An electromagnetic wave generator 200 that may be included in the second module 20 may be selected depending on the kind of the valve material V1 used in the cartridge 70.

Figure 4A:
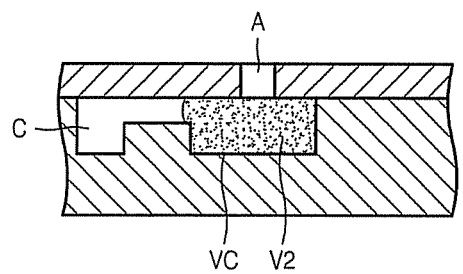
FIGS. 4A and 4B illustrate an exemplary operation of a closing valve.
Figure 4B:
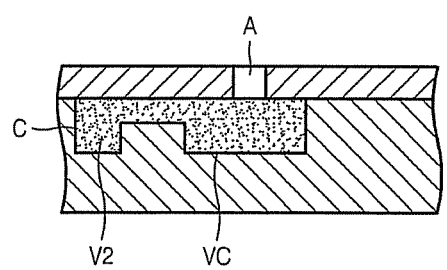

FIGS. 4A and 4B are cross-sectional views illustrating an exemplary operation of a closing valve. Referring to FIG. 4A, a closing valve may comprise a channel C, a valve chamber Vc connected to a portion of the channel C, and a valve material V2 which is filled in the valve chamber Vc through an injection hole A. In one exemplary embodiment, the valve material V2 may be made of a material identical to or different from the valve material V1 (FIG. 3) of the opening valve. Because the valve material V2 is in the valve chamber Vc before energy is applied from outside, the channel C may be maintained in an open state open.

Referring to FIG. 4B, when energy is applied from outside, the valve material V2 may be melted and expanded. The melted and expanded valve material V2 may flow toward the channel C. As the valve material V2 is solidified in the channel C, the flow of fluid through the channel C may be blocked.

Figure 5A:
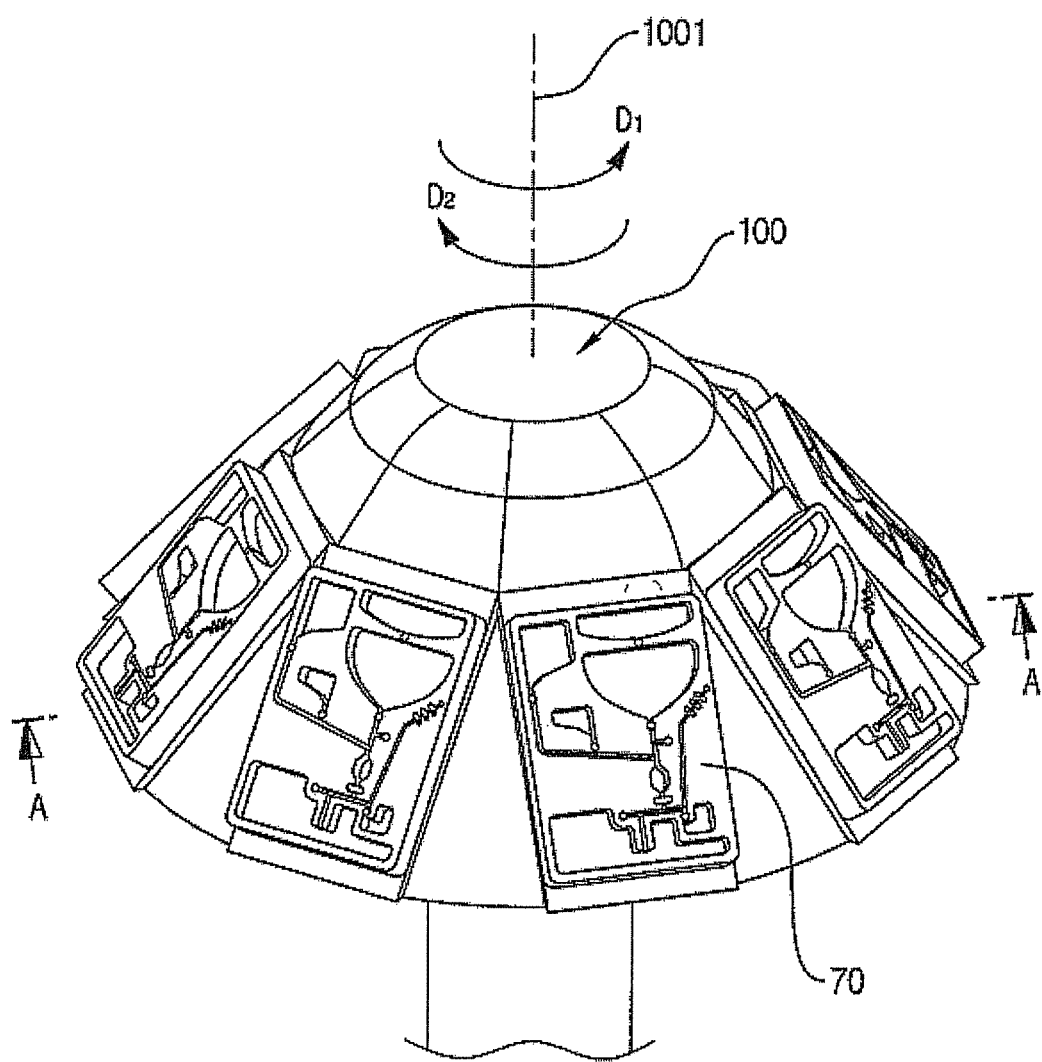
FIG. 5A is a front perspective view illustrating an exemplary embodiment of the coupling of a rotor and the exemplary embodiments of the cartridges in an exemplary embodiment of a system for processing a target material.
Figure 5B:
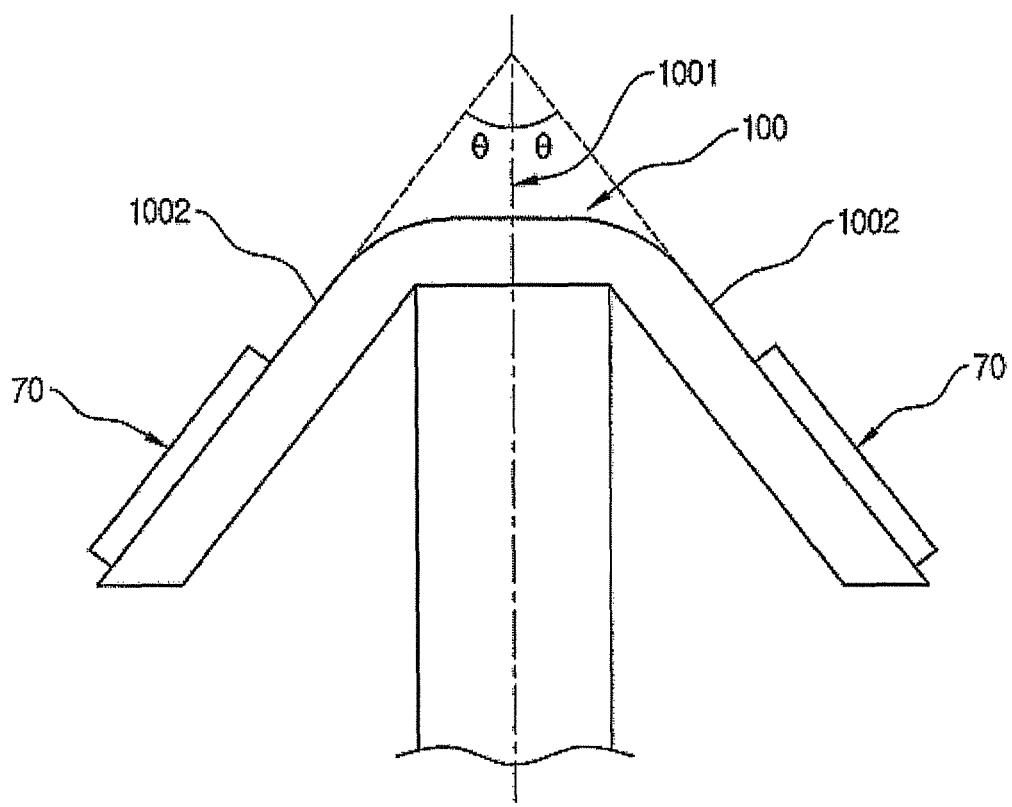
FIG. 5B is a cross-sectional view taken along line A-A' in FIG. 5A.

FIG. 5A is a schematic view illustrating the coupling of a rotor 100 and cartridges 70 in an exemplary embodiment of a system for processing a target material, and FIG. 5B is a cross-sectional view taken along line A-A' in FIG. 5A. In FIGS. 5A and 5B, the shape of the rotor 100 is shown simply for illustrating the coupling of the rotor 100 and cartridges 70, and other shapes would be equally applicable. Those skilled in the art will understand that the actual shape of the rotor 100 may be different from that shown in FIGS. 5A and 5B.

Referring to FIG. 5A, at least one cartridge 70 may be mounted on the rotor 100. The rotor 100 may be connected to the motor 101 (see FIG. 1), and may rotate around an axis of rotation 1001. The rotor 100 may rotate in one direction (e.g. direction D1 "counter-clockwise" or D2 "clockwise") along the rotating axis 1001. Alternative exemplary embodiments include configurations wherein the rotor 100 may rotate around the rotating axis 1001 in both directions D1, D2 alternatingly. In the exemplary embodiment the rotor 100 rotates alternatingly in both directions, a rotating angle in each direction may be about 0.1 degrees to about 30 degrees. Exemplary embodiments include configurations wherein the rotating angle of the rotor 100 in each direction may be identical or different. The rotating direction of the rotor 100 may be changed with a predetermined period. In on exemplary embodiment, the rotating direction of the rotor 100 may be changed according to a frequency of about 1 HZ to about 100 Hz.

Referring to FIG. 5B, the rotor 100 may have a surface 1002 on which the cartridge 70 is mounted. The surface 1002 of the rotor 100 on which the cartridge 70 is mounted may be inclined with respect to the rotating axis 1001. That is, the surface 1002 on which the cartridge 70 is mounted may form a predetermined angle θ with respect to the rotating axis 1001. The angle θ may be any angle from about 0 degrees to about 90 degrees. In one exemplary embodiment, the angle θ may be about 30 degrees to about 60 degrees.

Figure 6:
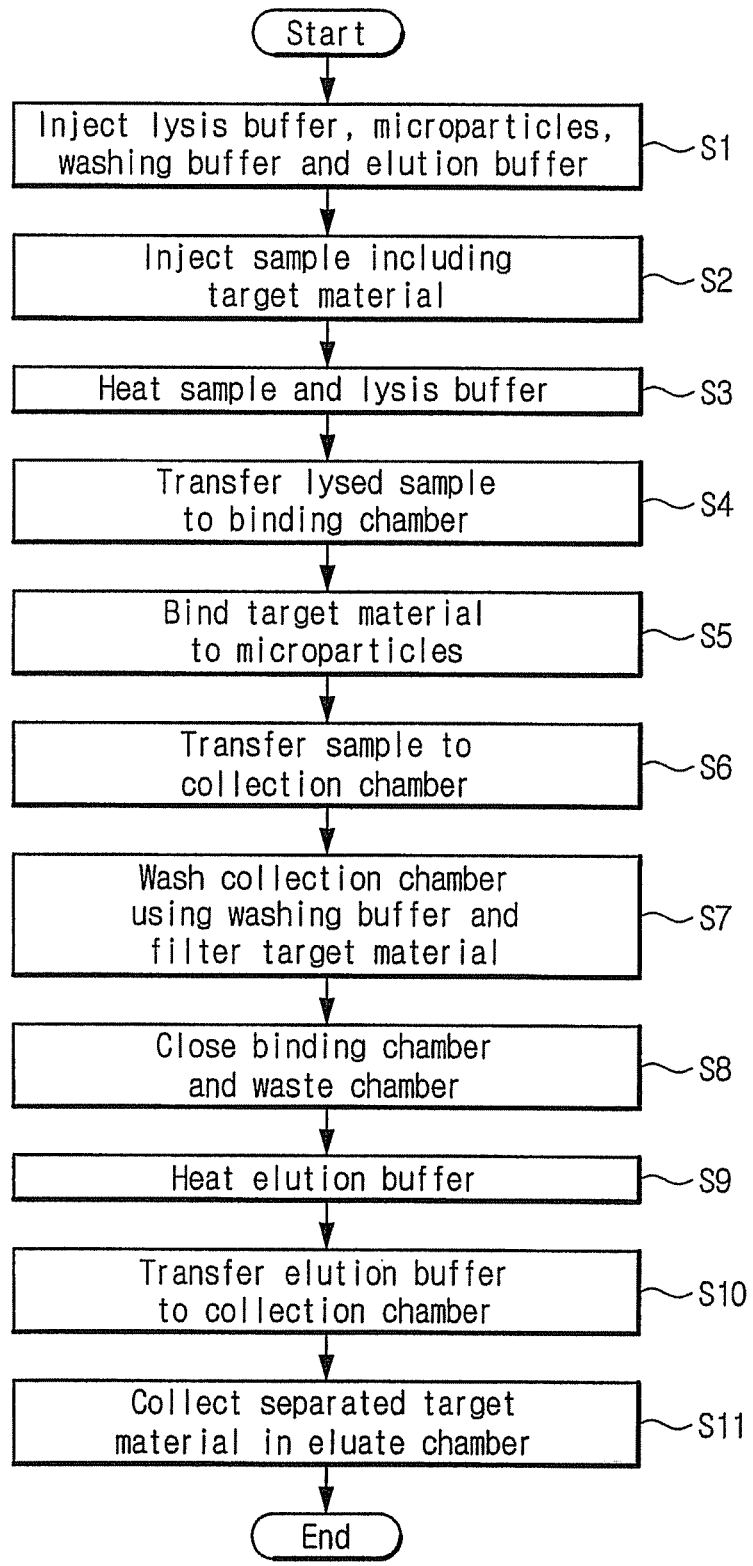
FIG. 6 is a flow chart of an exemplary embodiment of a method for processing a target material.

FIG. 6 is a flow chart of an exemplary embodiment of a method for processing a target material. FIG. 6 shows an exemplary method for processing a target material in which the target material is nucleic acid.

For convenience of explanation, the method for processing a target material will be described referring to FIGS. 1, 2 and 6. In one exemplary embodiment, a lysis buffer, binding buffer containing micro particles, a washing buffer and an elution buffer may be injected in the lysis chamber 701, the binding chamber 702, the washing chamber 704 and the elution chamber 706 of the cartridge 70, respectively (S1).

The lysis buffer may be a substance for lysing the cell membrane or cell wall of the cells included in a sample to expose the nucleic acid within. In one exemplary embodiment, the lysis buffer may include sodium acetate or other suitable substances. The micro particles may be a material which specifically captures the exposed nucleic acid. In one exemplary embodiment, the micro particles may be beads having a charge-reversible surface ("CRS") the charge polarity of which changes depending on acidity (pH) of the solution. In one exemplary embodiment, the beads having a CRS may include cationizable materials such as amine-based substances, and anionizable materials such as carboxy-based substances. Further, they may include materials which exhibit positive charge below a predetermined acidity and exhibit negative charge above the predetermined acidity.

The washing buffer may be a substance for washing out byproducts other than the micro particles and nucleic acids. In one exemplary embodiment, the washing buffer may include Tris-HCl or other suitable substances. The elution buffer may be a substance for separating the nucleic acids bound to the micro particles. In one exemplary embodiment, the elution buffer may include Tris-HCl-EDTA (ethylenediaminetetraacetic acid) buffer or other suitable substances.

Next, the sample including nucleic acid may be injected in the lysis chamber 701 (S2). At this time, the first module 10 loaded with the cartridge 70 may be repeatedly rotated clockwise and counterclockwise, so that the lysis buffer is mixed well with the sample. Next, the lysis chamber 701 may be heated, so that the sample is lysed (S3). In one exemplary embodiment, the lysis chamber 701 may be heated by positioning the temperature regulating block 300 of the third module 30 close to the lysis chamber 701. Exemplary embodiments include configurations wherein the temperature regulating block 300 is positioned in proximity to the lysis chamber 701 while the lysis chamber 701 is rotating, or when the lysis chamber has been stopped.

When the sample is lysed and the nucleic acid is exposed, the sample may be transferred to the binding chamber 702 (S4). First, an electromagnetic wave may be applied to the first valve 711 using the electromagnetic wave generator 200 of the second module 20. When an electromagnetic wave is applied to the first valve 711, the valve material V1 constituting the first valve 711 may be melted. Then, as the cartridge 70 is rotated, the melted valve material V1 may be transferred by centrifugal force into either the lysis chamber 701 or the binding chamber 702, and the first valve 711 may be opened. Accordingly, the sample in the lysis chamber 701 may be transferred to the binding chamber 702.

When the sample is transferred to the binding chamber 702, the nucleic acid in the sample may be bound to the micro particles in the binding chamber 702. In one exemplary embodiment, the nucleic acid may be bound to the micro particles by repeatedly rotating the cartridge 70 clockwise and counterclockwise using the second module 20.

When the nucleic acid is bound to the micro particles, the sample including the same may be transferred to the collection chamber 703 (S6). First, an electromagnetic wave may be applied to the second valve 712 to melt the valve material V1. Then, by rotating the cartridge 70, the sample in the binding chamber 702 may be transferred to the collection chamber 703 via the channel 741. A filter 720 may be equipped at the exit of the collection chamber 703. The filter 720 may be a device which blocks the micro particles and passes only the fluid. In one exemplary embodiment, the filter 720 may include glass wool. The nucleic acid bound to the micro particles may not pass through the filter 720 but may be collected in the collection chamber 703.

Next, the washing buffer in the washing chamber 704 may be transferred to the waste chamber 705 via the collection chamber 703 (S7). The washing buffer in the washing chamber may be transferred to the waste chamber 705 via the channel 743 by applying an electromagnetic wave to the third valve 713 and rotating the cartridge 70. As the washing buffer passes through the collection chamber 703, byproducts other than the nucleic acid and the micro particles may be transferred to the waste chamber 705 passing through the filter 720. However, because the nucleic acid bound to the micro particles cannot pass through the filter 720, only the micro particles and the nucleic acid bound to the micro particles may remain in the collection chamber 703.

In order to prevent the flow of the micro particles and the nucleic acid in the collection chamber 703 back to the binding chamber 702 in the following process, an electromagnetic wave may be applied to the fourth valve 714 to close the exit of the binding chamber 702 (S8) along the channel 741. Further, in order to prevent the transfer of the micro particles and the nucleic acid to the waste chamber 705, an electromagnetic wave may be applied to the fifth valve 715 to close the exit of the waste chamber 705 (S8).

Next, the elution chamber 706 in which the elution buffer is stored may be heated (S9). In one exemplary embodiment, the temperature regulating block 300 of the third module 30 may be positioned close to the elution chamber 706 to heat the elution chamber 706. When the elution buffer in the elution chamber 706 is heated, the elution buffer may be used to separate the nucleic acid from the micro particles. By applying an electromagnetic wave to the sixth valve 716 positioned at the exit of the elution chamber 706 and rotating the cartridge 70, the elution buffer may be transferred to the collection chamber 703 (S10). The charge polarity of the micro particles may be changed due to the introduction of the elution buffer. As a result, the nucleic acid may be separated from the micro particles. A passive valve 730, which is opened at a predetermined pressure or above, may be used so that the micro particles are sufficiently soaked in the elution buffer.

The nucleic acid separated from the micro particles may be transferred to the eluate chamber 707 (S11). The fluid including the nucleic acid in the collection chamber 703 may be transferred to the eluate chamber by applying an electromagnetic wave to the seventh valve 717 positioned at the inlet of the eluate chamber 707 and rotating the cartridge 70.

The process of extracting nucleic acid from a sample using an exemplary embodiment of a system for processing a target material has been described above. The system for processing a target material may be applied for the separation of nucleic acids including plasmid DNA, because it is possible to apply a centrifugal force by rotating the cartridge. In addition, the system for processing a target material may be used to extract or analyze different target materials, depending on the cartridge structure and the kind of reagent stored in the cartridge. Exemplary embodiments include configurations wherein the system for processing a target material may be applied for PCR or other processes.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

What is claimed is:

1. A system for processing a target material comprising:
   a cartridge which stores a material which reacts with the target material, and comprises a lower plate that comprises a substrate having, within the substrate, at least one chamber and at least one valve connected to the at least one chamber and further comprises an upper plate disposed upon the lower plate;
   a first module loaded with the cartridge and which rotates; wherein the first module comprises:
   a rotor on which the cartridge is mounted;

a motor which rotates the rotor;
a second module which selectively controls the at least one valve;
a third module which selectively controls the temperature of a selected chamber of the at least one chamber, the third module comprising a first transfer unit which includes a temperature regulating block mounted thereon and which moves with respect to the cartridge; and
a control module which controls the first module, second module and third module,
wherein the rotor has a surface on which the cartridge is mounted, and the surface on which the cartridge is mounted is inclined with respect to an axis of rotation of the rotor.

2. The system for processing a target material according to claim 1, wherein the surface on which the cartridge is mounted is inclined at an angle of about 30 to about 60 degrees with respect to the axis of rotation of the rotor.

3. The system for processing a target material according to claim 1, wherein the motor alternately changes a direction of rotation of the rotor in clockwise and counter clockwise directions and rotates the rotor.

4. The system for processing a target material according to claim 3, wherein an angle of rotation of the rotor in each direction is from about 0.1 degree to about 30 degrees.

5. The system for processing a target material according to claim 3, wherein the motor changes the direction of rotation of the rotor at a frequency of about 1 Hz to about 100 Hz.

6. The system for processing a target material according to claim 1, wherein the first module further comprises:
an encoder connected to the motor, and which generates a signal corresponding to the rotation of the motor; and
a first controller controlled by the control module, and which controls the motor using the signal generated by the encoder.

7. The system for processing a target material according to claim 1, wherein the second module comprises:
an electromagnetic wave generator which generates an electromagnetic wave and irradiates the at least one valve with the electromagnetic wave.

8. The system for processing a target material according to claim 7, wherein the second module further comprises:
a second transfer unit which includes the electromagnetic wave generator mounted thereon and which moves with respect to the cartridge; and
a second controller which is controlled by the control module, and controls the electromagnetic wave generator and the second transfer unit.

9. The system for processing a target material according to claim 1, wherein the third module further comprises:
a sensor which measures the temperature of the temperature regulating block; and
a third controller which is controlled by the control module, and controls the temperature of the temperature regulating block depending on the temperature measured by the sensor.

10. The system for processing a target material according to claim 1, further comprising:
a fourth module which takes photographs of the cartridge and transfers the photographs to the control module.

11. The system for processing a target material according to claim 1, further comprising:
a fifth module which controls the temperature of substantially the whole cartridge and is controlled by the control module.

12. The system for processing a target material according to claim 1, further comprising:
a sixth module which measures the concentration of the target material in the cartridge in an optical manner.

13. The system for processing a target material according to claim 1, wherein the target material includes nucleic acid.

14. The system for processing a target material according to claim 1, wherein the cartridge includes a plurality of chambers and a plurality of valves disposed between the plurality of chambers.

15. A method for processing a target material comprising:
injecting a material which reacts with the target material in a cartridge comprising a lower plate that comprises a substrate having, within the substrate, at least one chamber and at least one valve connected to the at least one chamber and further comprising an upper plate disposed upon the lower plate;
loading the cartridge onto a rotor that rotates the cartridge;
injecting a sample including the target material into the cartridge;
rotating the cartridge;
selectively controlling the at least one valve connected to the at least one chamber to transfer the target material from the at least one chamber; and
selectively controlling the temperature of a selected chamber of the at least one chamber by moving a temperature regulating block with respect to the cartridge,
wherein the rotor has a surface on which the cartridge is mounted, and the surface on which the cartridge is mounted is inclined with respect to an axis of rotation of the rotor.

16. The method for processing a target material according to claim 15, further comprising:
controlling the temperature of substantially the whole cartridge.

17. The method for processing a target material according to claim 15, wherein the selectively controlling the at least one valve comprises:
irradiating the valve with an electromagnetic wave.

18. The method for processing a target material according to claim 15, wherein the target material includes nucleic acid.

* * * * *